United States Patent [19]
Bokros

[11] 3,971,134
[45] July 27, 1976

[54] CARBON DENTAL IMPLANT WITH ARTIFICIAL PERIODONTAL LIGAMENT

[75] Inventor: Jack C. Bokros, San Diego, Calif.

[73] Assignee: General Atomic Company, San Diego, Calif.

[22] Filed: Jan. 31, 1975

[21] Appl. No.: 545,996

[52] U.S. Cl. .............................. 32/10 A; 128/92 C
[51] Int. Cl.² ........................................ A61C 13/00
[58] Field of Search ...... 32/10 A; 128/92 C, 92 CA, 128/92 D, 334 R; 3/1, 1.9, 1.91, 1.92, 1.93

[56] References Cited
UNITED STATES PATENTS

| | | | |
|---|---|---|---|
| 3,314,420 | 4/1967 | Smith et al. | 32/10 A |
| 3,526,005 | 9/1970 | Bokros | 128/334 R |
| 3,605,123 | 9/1971 | Hahn | 32/10 A |
| 3,707,006 | 12/1972 | Bokros et al. | 32/10 A |
| 3,808,606 | 5/1974 | Tronzo | 32/10 A |
| 3,855,638 | 12/1974 | Pilliar | 32/10 A |

OTHER PUBLICATIONS

"Biomechanical and Biomaterial Considerations of Natural Teeth, Tooth Replacements, and Skeletal Fixation," Buch et al., Aerospace Report, No. ATR-74(7400)-1, Aerospace Corporation, Sept. 15, 1973.

"Porous Implant Systems for Prosthesis Stabilization," Honesy et al., Clinical Orthopaedics, No. 89, Nov.–Dec., 1972, pp. 220–235.

Primary Examiner—Louis G. Mancene
Assistant Examiner—Jack Q. Lever
Attorney, Agent, or Firm—Fitch, Even, Tabin & Luedeka

[57] ABSTRACT

A dental prothesis for permanent or prolonged implantation in a jawbone of a living body comprising a carbon root having specified properties including a modulus of elasticity of about $4\times10^6$ psi, and an adherent, porous polymeric coating having specified properties and which is adapted to interface with bone.

5 Claims, 1 Drawing Figure

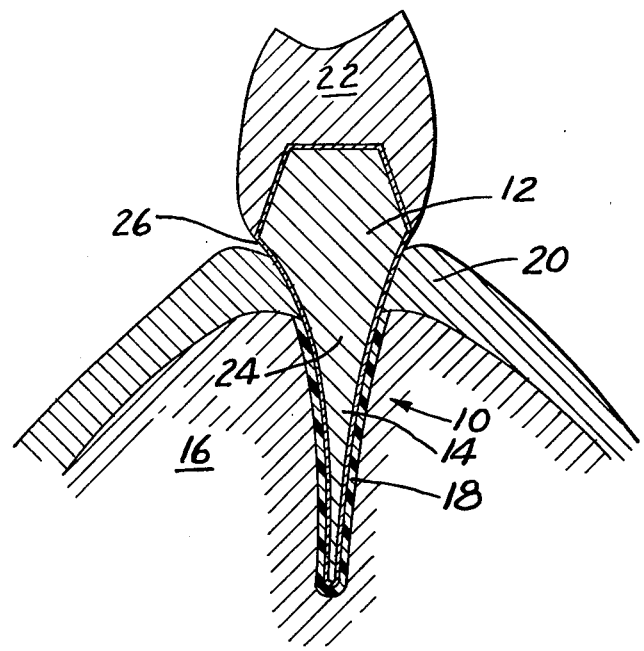

CARBON DENTAL IMPLANT WITH ARTIFICIAL PERIODONTAL LIGAMENT

The present invention is directed to periodontal implant devices, and more particularly is directed to an improved dental implant for direct appositional socket insertion.

Skeletal fixation of dental implant devices is an important problem which may be manifested clinically by adverse tissue response such as erosion, necrosis, and fibrous tissue formation at the site of skeletal attachment.

In natural teeth, the periodontal ligament is believed to play a significant role in the normal biomechanical toleration and dissipation of occlusional forces. It has been postulated that the natural periodontal ligament is under relatively little compressive stress parallel to its loading axis, such that it is primarily in a uniform state of shear.

Dental implants are commonly made of metal. However, assuming firm appositional attachment of a metal implant in a tooth socket, the stresses within the upper portion of the socket wall are lower than with the normal tooth and high stresses prevail at the bottom of the socket because of the higher stiffness of metal relative to bone. This abnormal stress state may induce abnormal stress-related tissue response. For example, the superior aspect of the socket may resorb because of excessively low stresses being present (i.e., saucerization), while the abnormally high pressures at the apical root may cause necrosis, remodeling, or the formation of a fibrous cushion of tissue.

Acrylic materials have had longstanding use in dentistry, are less stiff than compact bone, and therefore cause much less "punching" than metal. However, assuming firm appositional attachment of an acrylic dental implant, there may be abnormally high stresses at the superior aspect of the socket because of the lower stiffness of acrylic materials relative to bone.

The use of metal-reinforced acrylic dental implants has been proposed because of theoretical stress analysis considerations which indicate that an appropriate combination of these two materials could result in a compromise stress pattern resembling that of a normal tooth.

Carbonaceous dental implants, as disclosed in U.S. Pat. No. 3,707,006 to Bokros et al., have been designed to have approximately the same modulus of elasticity as natural bone to deal with the problems of stress concentration at the natural bone-prosthesis interface, and which are provided with a carbon surface roughness which facilitates the provision of an attachment with the jawbone through natural bone tissue growth.

However, improvements in dental implants are desirable, and it is an object of the present invention to provide improved prostheses for implant dentistry. It is a further object to provide a dental implant which simulates the biomechanical stress patterns of a normal tooth at the tooth-periodontal ligament-jawbone interface. It is still another object of the invention to provide a dental implant which becomes firmly attached to the jawbone through natural tissue growth without various of the difficulties associated with ankylosis and calcification at the natural bone-prosthesis interface.

These and other objects of the present invention are more particularly set forth in the following detailed description and in the accompanying drawing, which is a cross-sectional side view of an embodiment of the dental implant of the present invention appropriately positioned in a tooth socket of a jawbone. As used herein, the term jawbone refers to either the upper or lower mandible.

In accordance with the present invention, an improved prosthetic implant is provided for long-term replacement of natural teeth.

As illustrated by the embodiment 10 of the drawing, the dental implant of the present invention comprises a carbon root 12 which is shown with its base portion 14 in position in a prepared tooth socket in healed bone 16 of a human mandible. The tooth socket is prepared to generally conform to the shape of the base 14 of the implant, and the base portion 14 in the illustrated embodiment is suitably shaped to minimize bone loss. In addition, as will be more fully described hereinafter, the base portion 14 also is provided with a thin, adherent coating 18 of a porous polymeric material.

The carbon root 12 of the dental implant extends a sufficient distance beyond the base portion 14, so that upon implantation the implant projects from the tooth socket through the gingiva 20 to provide an abutment for attachment of a dental crown 22. The crown 22 may be made of porcelain or other suitable material which may be fastened to the abutment in an appropriate manner such as by adhesive cement. In practice, it will generally be advisable to wait a period of time following insertion of the implant into the jawbone to permit tissue affixation thereto before application of a crown to the implant.

As indicated, the root portion 12 of the dental implant of the present invention is formed of carbon, and more particularly is formed from carbon having certain specific physical characteristics. In this regard, the carbon root should have a modulus of elasticity of from $3.0\times10^6$ psi to $6.0\times10^6$ psi, or generally about the modulus of natural bone, which is about $4\times10^6$ psi. In addition, the carbon root portion must also have a compressive strength in a direction along the axis of the root (along the direction of insertion into the jawbone) so as to support a compressive load of at least about 200 pounds, and preferably at least about 300 pounds. Furthermore, the carbon root should have a flexural strength along the root axis to support a bending moment of at least about 20 inch-pounds, and preferably at least about 40 inch-pounds.

In the illustrated embodiment, the carbon root 12 has a composite structure comprising an artificial graphite substrate 24 having thereon a pyrolytically-deposited carbon coating 26. Artificial graphite materials have a modulus of elasticity of from about 2 to about $4\times10^6$ psi, which is ordinarily in the range of that of natural living bone. A particularly preferred form of graphite for use as a substrate material is polycrystalline graphite. An example of such a graphite is the polycrystalline graphite sold under the trade name POCO AXF Graphite, which has a density of about 1.9 grams per cubic centimeter, an average crystallite size of about 300 A, an isotropy of nearly 1.0 on the Bacon scale, and a modulus of elasticity of about $1.7\times10^6$ psi.

As indicated, the artificial graphite of the illustrated embodiment is provided with a pyrolytically-deposited carbon coating 26. As taught in U.S. Pat. No. 3,707,006 issued Dec. 26, 1972 to Bokros et al., it has been found that various prosthetic devices including dental implant devices having improved characteristics can be made by coating artificial graphite substrates of the desired shape and size with pyrolytic carbon. The use of pyrolytic carbon as a coating for prosthetic devices generally is disclosed in U.S. Pat. No. 3,526,005, issued Sept. 1, 1970, also to Bokros et al. Both of said patents are hereby incorporated by reference. Preferably, isotropic pyrolytic carbon is used which has a B.A.F. of about 1.3 or less, as defined in the Journal of Applied Chemistry, Vol. 6, p. 477, (1956). For purposes of explanation, it is noted that a B.A.F. of 1.0 (the lowest point on the B.A.F. scale) signifies perfectly isotropic carbon, while higher values indicate increasing degrees of anisotropy.

The density of the pyrolytic carbon is related to the additional strength which the pyrolytic carbon coating 26 will provide the substrate 24 and to the strength and modulus of elasticity contribution to the composite structure which results in the structure having a modulus of about $4\times10^6$ psi. The pyrolytic carbon should at least have a density of about 1.5 grams per cubic centimeter and preferably between about 1.9 grams/cm$^3$ and about 2.2 grams/cm$^3$.

As indicated, the base portion 14 of the dental implant of the illustrated embodiment is shaped so that bone tissue will be conserved upon preparation of a conforming socket in the jawbone for implantation of the base. While the illustrated embodiment has a smooth tapered base, the base may also have other shapes such as threaded screw-like shapes, conical shapes and blade shapes. In addition, the dental implant root may be machined to have the same profile as an extracted tooth and may be implanted in the cavity left after extraction.

The dental implants of the present invention are also provided with a biologically inert porous polymeric coating 26 adherently affixed to the base portion of the carbon root to serve as an artificial periodontal ligament. The porous polymeric coating should have a thickness of from about 0.1 mm. to about 1.0 mm. Furthermore, it is important that the porous polymeric material have a structure which permits attachment of the polymer coating to the adjacent bone tissue of the implant socket through natural tissue growth, while maintaining the relative resiliency of the polymeric layer. In this connection, the material of the porous polymeric coating may be provided with an accessible (interconnected) pore structure having a pore size generally in a range greater than about 10 microns so that the natural tissue of the tooth socket into which the root is to be inserted will attach to it, but less than a limit thought to be about 100 microns so that calcification will not occur within the porous coating upon prolonged implantation. Such a pore structure permits soft tissue attachment while inhibiting calcification, and in this connection the pore size will preferably be in a range between about 20 and about 50 microns. The porosity will generally extend at least 0.1 mm. into the polymeric coating of the root base, and for the minimal polymer layer thickness of 0.1 mm, will accordingly extend through the entire layer. The noncalcifying pore structure may extend through the entire coating thickness of coatings which are thicker than 0.1 mm. In another embodiment, the polymeric coating may be provided with a zone of surface-limited accessible porosity having a thickness which is at least equal to its pore size and having a pore size in a range of from about 150 to about 300 microns, which permits tissue ingrowth and calcification therein. In such an embodiment there should be at least 0.1 mm. of nonporous polymer between the surface-limited porosity and the surface of the base end of the carbon root so that the effective resiliency of the polymer layer will be retained upon prolonged implantation. In addition to a porous structure which permits natural tissue growth while retaining resiliency, the porous coating will also generally have a modulus of elasticity which is substantially less than that of the carbon root. More particularly, the porous polymeric material should have a bulk modulus of elasticity of about an order of magnitude less than that of the carbon root, or from about $1\times10^5$ to about $5\times10^5$ psi., and preferably about $3\times10^5$ psi. Moreover, the porous zone of the polymer coating (the entire polymer coating if the porosity extends through the entire thickness of the coating) will have a volume percentage of accessible porosity of from about 10 percent to about 50 percent. Examples of suitable porous polymeric materials are resilient, high porosity composites of polytetrafluoroethylene and carbon fibrils, such as referred to by the trade designation "Proplast" (see "Rebuild with Proplast and Tissue Has a Home", Medical World News, Sept. 29, 1972, and "Pilot Studies of a Porous Implant in Dentistry", Journal of Oral Surgery, Vol. 30, August, 1972). Other biologically inert, porous organopolymeric materials, such as porous acrylic polymers such as polymethylmethacrylate, polyethylene and polytetrafluoroethylene, may also be employed. The implant will become firmly attached to the mandible through natural tissue growth over a period of time, and through the provision of the porous polymeric layer which prevents calcification therein, the implant is provided with an artificial periodontal ligament which does not lose its effectiveness after prolonged periods of implantation.

As indicated, the porous polymeric material covers the base portion of the carbon root of the implant so that it is disposed to interface with the natural bone of the tooth socket into which the root is to be implanted. However, it is important that upon implantation, the covered area of the root interface only with the bone of the tooth socket and not with the gingival tissues, so that it does not extend through the skin. In this regard, such a construction prevents the ingress of bacteria which could defeat the viability of the implant.

The present invention provides an improved dental implant for prolonged or permanent implantation, having an artificial periodontal ligament and which becomes firmly attached to the jawbone through natural tissue growth without various of the difficulties associated with ankylosis and calcification at the jawbone-implant interface.

While the present invention has been described with particularity with respect to a particular embodiment, it will be appreciated by those skilled in the art that various modifications may be made without departing from the teachings of the present disclosure.

What is claimed is:

1. A prosthesis for dental replacement in a living body comprising a carbon root having an abutment adapted for affixation of a dental crown thereto, and having a base portion shaped for insertion into a mandible tooth socket, said carbon root having a modulus of elasticity of from about $3\times10^6$ psi. to about $6\times10^6$ psi., a compressive strength along its axis sufficient to support a compressive load of at least 200 pounds, and a flexural strength along its axis to support a bending moment of at least 20 inch-pounds, said base portion of said carbon root having a biologically inert, porous organopolymeric coating thereon with a thickness of from about 0.1 to about 1.0 mm and a bulk modulus of elasticity of from about $1 \times 10^5$ psi. to about $5 \times 10^5$ psi., said organopolymeric coating having a pore structure extending at least 0.1 mm. into said organopolymeric coating and which permits attachment of tissue thereto through tissue ingrowth while retaining the resiliency of the polymer layer, the pore structure of said organopolymeric coating having a volume percentage of accessible porosity of from about 10 to about 50 percent, and said organopolymeric coating being limited to said base portion of said carbon root which is intended to interface with bone upon implantation.

2. A dental implant prosthesis according to claim 1 wherein said porous organopolymeric coating has a noncalcifying pore structure having a pore size in a range of from about 10 to about 100 microns.

3. A dental implant prosthesis according to claim 1 wherein said polymeric coating is formed from a material selected from the group consisting essentially of acrylic polymers, polyethylene, and polytetrafluoroethylene-carbon fibril compositions.

4. A dental implant prosthesis according to claim 1 wherein said organopolymeric coating is provided with a surface zone of accessible porosity having a thickness which is at least equal to its pore size and having a pore size in a range of from about 150 to about 300 microns which permits tissue ingrowth and calcification therein, and wherein there is at least 0.1 mm of nonporous organopolymeric coating between said porous surface zone and said base portion of said carbon root to provide for retention of resiliency upon prolonged implantation.

5. A dental implant prosthesis according to claim 2 wherein said carbon root has a composite structure comprising an artificial graphite substrate having a modulus of elasticity of from about 2 to about $4 \times 10^6$ psi. and a pyrolytically deposited carbon coating having a B.A.F. of about 1.3 or less and a density of between about 1–9 grams/cm$^3$ and about 2.2 grams/cm$^3$.

* * * * *